United States Patent [19]

Tahara et al.

[11] 4,265,910

[45] May 5, 1981

[54] ISOPRENYLAMINES

[75] Inventors: Yoshiyuki Tahara, Ohi; Hiroyasu Koyama, Ageo; Yasuhiro Komatsu, Niiza; Reiko Kubota, Tokyo; Toshihiro Takahashi, Kamifukuoka, all of Japan

[73] Assignee: Nisshin Flour Milling Co., Ltd., Tokyo, Japan

[21] Appl. No.: 145,754

[22] Filed: May 1, 1980

[30] Foreign Application Priority Data

May 4, 1979 [JP] Japan .............................. 54-54016
Nov. 19, 1979 [JP] Japan ............................ 54-148819

[51] Int. Cl.$^3$ ........................ A61K 31/13; C07C 87/24
[52] U.S. Cl. ...................................... 424/325; 564/509
[58] Field of Search ......................... 564/509; 424/325

[56] References Cited

U.S. PATENT DOCUMENTS

| 3,444,202 | 5/1969 | Chung et al. | 564/509 X |
| 3,732,282 | 5/1973 | Henrick et al. | 424/325 X |
| 3,773,833 | 11/1973 | Henrick et al. | 564/509 |
| 3,786,097 | 1/1974 | Karrer | 424/325 X |
| 3,801,652 | 4/1974 | Rüegg et al. | 564/509 X |
| 3,824,290 | 7/1974 | Henrick | 424/325 X |

FOREIGN PATENT DOCUMENTS 53-95912  8/1978  Japan ........................................ 560/129

*Primary Examiner*—John Doll
*Attorney, Agent, or Firm*—Haseltine and Lake

[57] ABSTRACT

This invention relates to new isoprenylamines and the acid addition salts thereof. Further, the invention is concerned with antiviral agents for vertebrate animal, said agents containing as their active ingredients isoprenylamine or physiologically acceptable acid addition salt thereof.

5 Claims, No Drawings

ISOPRENYLAMINES

There are known heretofore various substances, which have been decided to have preventive or alleviative effects on diseases caused by virus whose host is a vertebrate animal, or which have been recognized to be capable of alleviating symptoms of the diseases by significantly enhancing antibody activity in the animal. Antivirotics reported so far include interferon, substances capable of inducing interferon, i.e. inducers (interferon inducers), amantadine hydrochloride or synthetic substances, such as methysazone, which directly exert inhibitory effect on the virus propagation. Interferon is glycoprotein having antiviral and antitumor activity, said glycoprotein being produced in situ by cells of vertebrate animal when the cells are infected with virus, and has been suggested for the therapy of infectious viral diseases and also for the therapy of cancer. Known inducers, which induce interferon in vertebrate animals by a process other than the virus infection, include natural high molecular substances such as double chain ribonucleic acid of bacteriophage of a certain species, or synthetic high molecular substances such as double chain ribonucleic acid, typical of which is polyinosinic acid-polycytidylic acid, or low molecular inducers such as tyrolone.

However, in the production of interferon there is involved a problem how to carry out the purification thereof, and in fact no economical process for the production thereof has not been established yet. On the other hand, conventional interferon inducers have not been put to practical use mainly because of toxicity thereof. Synthetic antiviral agents which directly exert inhibitory effect on the virus propagation, which are commercially available at present, have a rather narrow range of virus-infected diseases which are curable by administration of said agent, and thus the advent of novel synthetic antiviral agents is earnestly desired. Taking such circumstances into consideration, the present inventors extensively conducted studies in finding compounds capable of producing interferon of high potency and, moreover, have antiviral activity on the biological level, and as the result they have eventually have found that compounds represented by the following general formula (I) and acid addition salts thereof show excellent interferon inducing ability and, at the same time, demonstrate excellent antiviral activity even in the biological test.

Thus, the one aspect of the present invention is to provide a new class of isoprenylamines represented by the following general formula

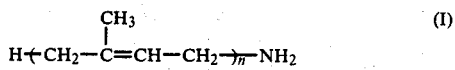

wherein n is 9, 10 or 11, and acid addition salts thereof.

For the production of isoprenylamine represented by the above-mentioned general formula (I) and acid addition salts thereof, there may be adopted a process in which a known process for the amine synthesis is applied, for example, to the starting isoprenyl alcohol, i.e. nonaprenol (solanesol), decaprenol or undecaprenol, represented by the following general formula and thereby to produce a corresponding amine.

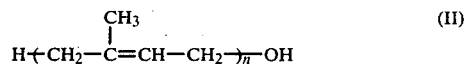

wherein n is 9, 10 or 11.

Further, the amine thus obtained may be converted into a corresponding salt in the usual way. More particularly, a desired amine can be produced according to a process which comprises converting a suitable isoprenyl alcohol of the aforesaid general formula (II) into a corresponding halide or sulfonic acid ester, followed by reacting the compound thus converted (i) with ammonia directly, (ii) with a protected amine (e.g. potassium phthalimide), followed by removal of the protective group, or (iii) with hexamethylenetetramine or guanidine to obtain a corresponding salt, and hydrolyzing the corresponding amine. An acid addition salt of the amine thus obtained can be obtained by mixing said amine in an appropriate solvent with a desired acid to form a sat and crystallizing the salt out of the solution by evaporation or other means to recover the same. The acid addition salts suitable for use as medicines include, for example, those with hydrochloric acid, acetic acid, citric acid, fumaric acid and the like.

The compounds represented by the general formula (I) and acid addition salts thereof are illustrated below with reference to preparative example.

PREPARATIVE EXAMPLE 1

A mixture comprising 17.4 g of solanesyl bromide, 5.6 g of potassium phthalimide and 70 ml of N,N-dimethylformamide was stirred for 2 hours, followed by stirring at 60° C. for an additional hour. Insoluble matters were separated by filtration, and the filtrate was concentrated under reduced pressure. The residue was dissolved in ethyl acetate, washed successively with water and saturated brine, dried over anhydrous sodium sulfate and then concentrated under reduced pressure. The residue was purified by means of silica gel chromatography (eluted with a mixture of n-hexane and benzene) to obtain 12,8 g of N-solanesyl phthalimide (yield, 67%, m.p., 51°–53° C.).

Subsequently, 5 g of N-solanesyl phthalimide thus obtained was added to a mixture of 0.42 ml of hydrazide (85% pure, hydrated form) and 40 ml of a 95% ethanol solution, and the mixture was heated under reflux in a nitrogen stream for 2 hours with stirring and then cooled. The mixture was treated while stirring with a solution of 1.9 g of potassium hydroxide in 11 ml of water. The deposited oily product was extracted twice with ether. The ethereal layer was washed successively with water containing a small amount of potassium carbonate and saturated brine, dried over an hydrous sodium sulfate containing a small amount of potassium carbonate, and then concentrated under reduced pressure. The oily product thus treated was dissolved in 40 ml of acetone, to which was added with ice-cooling and stirring 5 N hydrogen chloride-ethanol solution until the solution was made weakly acidic. The deposited crystals were collected by filtration and recrystallized from acetone containing a small amount of ethanol to obtain 2.2 g of solanesylamine hydrochloride (yield, 50%, m.p., 57°–59° C.).

Elementary analysis for $C_{45}H_{76}NCl$:

|  | C % | H % | N % |
|---|---|---|---|
| Calculated: | 81.09 | 11.49 | 2.10 |
| Found: | 80.61 | 11.44 | 2.18 |

PREPARATIVE EXAMPLE 2

Decaprenylamine hydrochloride was obtained starting from decaprenyl bromide by repeating the same procedures as in Example 1. The hydrochloride thus obtained had a melting point of 56°–58° C.

Elementary analysis for $C_{50}H_{84}NCl$:

|  | C % | H % | N % |
|---|---|---|---|
| Calculated: | 81.74 | 11.52 | 1.91 |
| Found: | 81.19 | 11.41 | 1.88 |

PREPARATIVE EXAMPLE 3

Undecaprenylamine hydrochloride was obtained starting from undecaprenyl bromide by repeating the same procedures as in Example 1. The hydrochloride thus obtained had a melting point of 55°–57° C.

Elementary analysis for $C_{55}H_{92}NCl$:

|  | C % | H % | N % |
|---|---|---|---|
| Calculated: | 82.29 | 11.55 | 1.74 |
| Found: | 81.70 | 11.64 | 1.75 |

According to another aspect of the present invention, the isoprenylamines and physiologically acceptable acid addition salts thereof are used as active ingredients to combat virus infections of vertebrate animals including human being. Thus, the present invention involves antiviral agents for vertebrate animals which contain as their active ingredients an isoprenylamine or the physiologically acceptable acid addition salt thereof.

Physiological effects of the active ingredients used in the present invention are illustrated below in detail with reference to test results as obtained.

(1) INTERFERON INDUCING ACTIVITY TEST

In the matter as indicated in Table 1, a solution of each test compound in a surfactant containing water was abdominally administered to each group consisting of 5 ICR female mice weighing about 25 g. After 20 hours, blood was drawn from the mice and serum was separated therefrom to obtain a serum interferon. The following steps were taken in order to determine potency of the serum interferon thus induced. L-929 cells derived from mice and incubated previously in a monolayer was brought into contact with the test serum solution diluted 10 times, incubated overnight at 37° C. in a carbon dioxide gas incubator and the dilute test serum solution was removed therefrom. Thereafter, the cells were inoculated with vesicular stomatitis virus and placed on a tissue culture medium containing 1% agar. After incubation at 37° C. for 24 hours, the cells were dyed with neutral red solution diluted to an appropriate concentration to count the number of plaques formed thereon and thereby to calculate the plaque inhibition rate in each of the test groups against a group to which no test compound had been administered. The plaque inhibition rate of each test compound is shown in Table 1.

TABLE 1

| Test compound | Dose | Plaque inhibition |
|---|---|---|
| Solanesylamine hydrochloride | 20 mg/kg | 81.0% |
| Solanesylamine hydrochloride | 40 mg/kg | 79.7% |
| Decaprenylamine hydrochloride | 20 mg/kg | 47.1% |
| Decaprenylamine hydrochloride | 40 mg/kg | 83.0% |
| Undecaprenylamine hydrochloride | 40 mg/kg | 70.3% |

(2) EFFECT ON MICE INFECTED WITH VACCINIA VIRUS

Groups, each consisting of 10 ICR female mice, were intravenously injected vaccinia virus (DIE strain) from the vein of tail. On the 8th day after the inoculation, the number of lesions in form of small pocks on the tail surface was counted after dyeing the tail with 1% fluorescein 0.5% methylene blue solution. In this test, each test compound was administered intraperitoneally, orally and/or subcutaneously to the mice on the day just before inoculation of the virus or for 6 days consecutively from the day of the virus challenge, whereby antivirus activity of the test compound was evaluated in terms of inhibition of tail lesions as calculated in each test group against a group to which no test compound had been administered.

TABLE 2

| Test compound | Administration Dose | Route | Inhibition of tail lesion Dosed one time | Consecutively dosed (6 times) |
|---|---|---|---|---|
| Solanesylamine hydrochloride | 20 mg/kg | i.p. | 35.7% | — |
|  | 30 mg/kg | i.p. | 72.1% | — |
|  | 30 mg/kg | s.c. | 23.2% | — |
|  | 40 mg/kg | p.o. | 40.5% | — |
| Decaprenylamine hydrochloride | 20 mg/kg | i.p. | 76.1% | 77.4% |
|  | 30 mg/kg | i.p. | 68.7% | — |
|  | 40 mg/kg | i.p. | 79.6% | 88.2% |
|  | 30 mg/kg | s.c. | 69.7% | — |
|  | 20 mg/kg | p.o. | — | 56.8% |
|  | 50 mg/kg | p.o. | 24.1% | — |
| Undecaprenylamine hydrochloride | 20 mg/kg | i.p. | 52.4% | — |
|  | 30 mg/kg | i.p. | 40.5% | — |
|  | 100 mg/kg | p.o. | 45.6% | — |

(3) EFFECT ON MICE INFECTED WITH INFLUENZA VIRUS

Groups, each consisting of 10 ICR female mice weighing about 25 g were challenged influenza virus A/PR-8 intratracheally. A solution of each test compound in an aqueous solution containing a surfactant was intraperitoneally administered to the mice 24 hours and 3 hours before the virus infection, and 5 times every other day from the second day after the infection. The mice that survived 21 days after the challenge were regarded as survivors, and survival rate was obtained according to the following equation.

TABLE 3

$$\frac{\text{Number of survivors}}{\text{Number of mice treated}} \times 100 = \text{survival rate}$$

| Test compound | Dose | Survival rate |
| --- | --- | --- |
| Solanesylamine hydrochloride | 20 mg/kg | 60% |
| Decaprenylamine hydrochloride | 40 mg/kg | 70% |
| Undecaprenylamine hydrochloride | 40 mg/kg | 30% |
| Control (Untreated) | — | 10% |

(4) HUMAN INTERFERON INDUCING ACTIVITY (IN VITRO)

Human fibroblast cells that had been incubated in a monolayer were brought into contact for 1 hour with a 1% ethanol solution of each test compound diluted with PBS (−). The test compound was removed and then the cells were subjected to superinduction (with cycloheximide and actinomycin D). After incubating overnight at 37° C., the supernatant was taken as a sample for interferon assay.

For interferon assay, the same cultured human fibroblast cells were brought into contact with the sample to be incubated overnight at 37° C. The incubated cells were then inoculated with vesicular stomatitis virus, and incubated with 3H-uridine overnight. Cell degradation rate was calculated from the radioactivity of RNA of cytolysed cells. The cell degradation rate thus measured was shown in Table 4.

TABLE 4

| Test compound | Dose (μg/well) | Inhibition of cytolysis (%) |
| --- | --- | --- |
| Solanesylamine hydrochloride | 5 | 55.4 |
| Decaprenylamine hydrochloride | 5 | 64.9 |
| Undecaprenylamine hydrochloride | 5 | 83.3 |

(5) TOXICITY

In order to investigate acute toxicity of the ingredients of the present invention, 50% lethal dose of each ingredient was obtained by intravenous and intraperitoneal administration thereof by ddY male mice weighing 20-25 g. From the results shown in Table 5, it is understood that the ingredients had high safety margin.

TABLE 5

| | 50% Lethal dose (mg/kg) | |
| --- | --- | --- |
| Test compound | Intravenously administered | Intraperitoneally administered |
| Solanesylamine hydrochloride | 32.3 | >500 |
| Decaprenylamine hydrochloride | 39.5 | 1000 |
| Undecaprenylamine hydrochloride | 18.0 | >1000 |

As is clear from the foregoing test results, the active ingredients of the present invention have interferon inducing activity in vivo and are low in toxicity. In the light of the fact that in the present ingredients, the strict correlation of interferon activity with the individual antivirus activities is not always observed for the present ingredients, there is considered also a possibility that the antivirus activities of said ingredients at biological level are concerned not only in interferon but also in other defensive mechanism of host. Accordingly, when the active ingredients of the present invention are used for treatment of virus-infected diseases, they are administered to patients by such techniques involving oral, inhalant, or the like administration and subcutaneous, intramascular and intravenous injection. According to the condition of patient such as age, symptom and route by which the ingredient is administered, the active ingredient of the present invention is used in a dose of 0.1-20 mg/kg, preferably 3-5 mg/kg several times (2-4 times) per day.

The active ingredients of the present invention can be formulated into compositions for medication, for example, tablets, capusules, granules, powder, liquid preparation for oral use, eye lotions, suppositories, ointments, injections and the like.

When the present active ingredients are orally administered, they may be formulated into tablets, capsules, granules or powder. These solid preparations for oral use may contain commonly used excipients, for example, silicic anhydride, metasilicic acid, magnesium alginate, synthetic aluminum silicate, lactose, cane sugar, corn starch, microcrystalline cellulose, hydroxypropylated starch or glycine, and the like; binders, for example, gum arabic, gelatin, tragacanth, hydroxypropyl cellulose or polyvinylpyrrolidone; lubricants, for example, magnesium stearate, talc or silica; disintegrating agents, for example, potato starch and carboxymethyl cellulose; or wetting agents, for example, polyethylene glycol, sorbitan monooleate, hydrogenated castor oil, sodium laurylsulfate. In preparing soft capsules, in particular, the present active ingredients may be formulated by dissolving or suspending them in commonly used oily substrates such as sesame oil, peanut oil, germ oil, fractionated coconut oil such as Miglyol ®, or the like. Tablet or granule preparations may be coated according to the usual method.

Liquid preparation for oral use may be in the form of aqueous or oily emulsion, solution or syrup, or alternatively in the form of dry product which can be re-dissolved before use by means of a suitable vehicle. To these liquid preparations, there may be added commonly used additives, for example, emulsifying aids such as sorbitol syrup, methyl cellulose, gelatin, hydroxyethyl cellulose and the like; or emulsifiers, for example, lecithin, sorbitan monooleate, hydrogenated castor oil, non-aqueous vehicles, for example, fractionated coconut oil, almond oil, peanut oil and the like; or antiseptics, for example, methyl p-hydroxybenzoate, propyl p-hydroxybenzoate or sorbic acid. Further, these preparations for oral use may contain, if necessary, preservatives, stabilizers and the like additives.

In case where the present active ingredients are administered in the form of non-oral suppository, they may be formulated according to the ordinary method using oleophilic substrates such as cacao oil or Witepsol ®, or may be used in the form of rectum capsule obtained by wrapping a mixture of polyethylene glycol, seame oil, germ oil, fractionated coconut oil and the like in a gelatin sheet. The rectum capsule may be coated, if necessary, with waxy materials.

When the present active ingredients are used in the form of injection, they may be formulated into preparations of oil solution, emulsified solution or aqueous solution, and these solutions may contain commonly used emulsifiers, stabilizers or the like additives.

According to the method of administration, the above-mentioned compositions can contain the present active ingredients in an amount of at least 1%, preferably 5 to 50%.

The procedure of formulating the present active ingredients into various preparations is illustrated below with reference to Pharmaceutical Examples.

PHARMACEUTICAL EXAMPLE 1

Hard capsule preparations for oral use

A mixture of 25 g of decaprenylamine hydrochloride and 7.5 g of polyoxyethylene castor oil in acetone was mixed with 25 g of silicic anhydride. After evaporation of the acetone, the mixture was mixed further with 5 g of calcium carboxymethylcellulose, 5 g of corn starch, 7.5 g of hydroxypropylcellulose and 20 g of microcrystalline cellulose, and 30 ml of water was added thereto and kneaded to give a granular mass. The mass was pelletized by means of a pelletizer (ECK pelletter of Fuji Paudal Co., Japan) equipped with No. 24 mesh (B.S.) screen to obtain granules. The granules were dried to less than 5% moisture content and screened with No. 16 mesh (B.S.) screen. The screened granules were capsuled by means of a capsule filling machine so as to be contained in an amount of 190 mg per capsule.

PHARMACEUTICAL EXAMPLE 2

Soft capsule preparations for oral use

A homogeneous solution was prepared by mixing 50 g of undecaprenylamine with 130 g of polyethylene glycol (Macrogol 400). Separately, a gelatin solution was prepared which contained 93 g of gelatin, 19 g of glycerine, 10 g of D-sorbitol, 0.4 g of ethyl p-hydroxybenzoate, 0.2 g of propyl p-hydroxybenzoate and 0.4 g of titanium oxide and which was used as a capsule film forming agent. The previously obtained solution, together with the capsule film forming agent, was treated with a manual type flat punching machine to obtain capsules each having the contents of 180 mg.

PHARMACEUTICAL EXAMPLE 3

Injections

A mixture of 5 g of decaprenylamine hydrochloride, an appropriate amount of peanut oil and 1 g of benzyl alcohol was made a total volume of 100 cc by addition of peanut oil. The solution was portionwise poured in an amount of 1 cc under asepsis operation into an ampule which was then sealed.

PHARMACEUTICAL EXAMPLE 4

Injections

A mixture of 1.0 g of decaprenylamine hydrochloride, 5.0 g of Nikkol HCO 60 (a tradename) (hydrogenated castor oil polyoxyethylene-60 mols-ether), 20 g of propylene glycol, 10 g of glycerol and 5.0 g of ethyl alcohol was mixed with 100 ml of distilled water and stirred. Under asepsis operation, the solution was portionwise poured in an amount of 1.4 ml into an ampule which was then sealed.

What we claim is:

1. Isoprenylamine represented by the following general formula

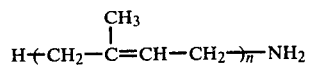

wherein n is 9, 10 or 11, or acid addition salts thereof.

2. Solanesylamine or acid addition salts thereof.
3. Decaprenylamine or acid addition salts thereof.
4. Undecaprenylamine or acid addition salts thereof.
5. An antiviral agent for vertebrate animal, characterized by containing as its active agent at least one member selected from the group consisting of isoprenylamine represented by the following general formula

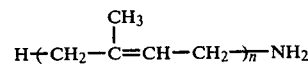

wherein n is 9, 10 or 11, or acid addition salts thereof.